(12) United States Patent
Agarwal et al.

(10) Patent No.: US 10,478,315 B2
(45) Date of Patent: Nov. 19, 2019

(54) APPARATUS AND METHOD FOR INJECTING BONE GRAFT SUBSTITUTE AND OTHER MATERIALS

(71) Applicant: The University of Toledo, Toledo, OH (US)

(72) Inventors: Anand K. Agarwal, Toledo, OH (US); Vijay K. Goel, Toledo, OH (US); Joel M. Gerber, Toledo, OH (US); Aakash Agarwal, Toledo, OH (US)

(73) Assignee: The University of Toledo, Toledo, OH (US)

( * ) Notice: Subject to any disclaimer, the term of this patent is extended or adjusted under 35 U.S.C. 154(b) by 352 days.

(21) Appl. No.: 15/320,803

(22) PCT Filed: Jun. 24, 2015

(86) PCT No.: PCT/US2015/037527
§ 371 (c)(1),
(2) Date: Dec. 21, 2016

(87) PCT Pub. No.: WO2015/200543
PCT Pub. Date: Dec. 30, 2015

(65) Prior Publication Data
US 2017/0196702 A1    Jul. 13, 2017

Related U.S. Application Data

(60) Provisional application No. 62/016,498, filed on Jun. 24, 2014.

(51) Int. Cl.
*A61F 2/46* (2006.01)
*A61M 5/145* (2006.01)
(Continued)

(52) U.S. Cl.
CPC ........ *A61F 2/4601* (2013.01); *A61B 17/8822* (2013.01); *A61B 17/8825* (2013.01);
(Continued)

(58) Field of Classification Search
CPC .......... A61F 2/46; A61F 2/4601; A61B 17/88; A61B 17/8822; A61M 5/145; A61M 5/14526; A61M 5/172
See application file for complete search history.

(56) References Cited

U.S. PATENT DOCUMENTS 5,425,716 A * 6/1995 Kawasaki ........... A61M 5/1456
128/DIG. 12
2004/0024361 A1* 2/2004 Fago ................ A61M 5/31525
604/152
(Continued)

FOREIGN PATENT DOCUMENTS

CN    100411696 C    8/2008
CN    101318037 A    12/2008

OTHER PUBLICATIONS

First Chinese Office Action, Application No. 201580042549.X, dated Mar. 22, 2019.

*Primary Examiner* — Christopher J Beccia
(74) *Attorney, Agent, or Firm* — MacMillan, Sobanski & Todd, LLC

(57) ABSTRACT

A metering delivery apparatus for injecting bone graft cement includes a body portion, a material containment vessel, an actuator, and a control unit. The body portion includes a drive housing that supports an actuator drivetrain and receiver end that supports the material containment vessel. The actuator has a first end connected to the actuator drivetrain and a second end that supports a moveable portion of the vessel to dispense material in the vessel and a retracting movement that relieves pressure applied to the material. The control unit receives actuator parameter inputs (Continued)

and includes a sensor to detect a signal of at least one of a pressure level and a time period. The sensor provides the detected signal to the control unit such that the control unit operates the actuator between the dispensing and retracting movements based on the detected signal and the actuator parameter inputs.

14 Claims, 8 Drawing Sheets

(51) Int. Cl.
*A61M 5/172* (2006.01)
*A61B 17/88* (2006.01)

(52) U.S. Cl.
CPC ........ *A61M 5/14526* (2013.01); *A61M 5/172* (2013.01); *A61M 2005/14513* (2013.01)

(56) References Cited

U.S. PATENT DOCUMENTS

| | | | | |
|---|---|---|---|---|
| 2008/0091207 | A1* | 4/2008 | Truckai | A61B 17/1671 |
| | | | | 606/79 |
| 2008/0306443 | A1* | 12/2008 | Neer | A61M 5/007 |
| | | | | 604/121 |
| 2011/0184281 | A1 | 7/2011 | Fago et al. | |

* cited by examiner

APPARATUS AND METHOD FOR INJECTING BONE GRAFT SUBSTITUTE AND OTHER MATERIALS

CROSS-REFERENCE TO RELATED APPLICATIONS

This application claims the benefit of U.S. Provisional Application No. 62/016,498, filed Jun. 24, 2014, the disclosure of which is incorporated herein by reference.

BACKGROUND OF THE INVENTION

Traditionally bone cement is mixed by hand or in a specialized cement mixer and inserted into a syringe. The syringe is then used to inject the cement into the desired location. Typically the injection process is done by hand. Some systems exist that aid in the injection process through the use of levers and ratchets, worm-screws and other mechanical devices. These systems reduce the force required for the injections resulting in less exertion by the surgeon.

SUMMARY OF THE INVENTION

This invention relates to a metering delivery apparatus having a body portion, a material containment vessel, an actuator, and a control unit. The body portion includes a drive housing that supports an actuator drivetrain and receiver end. The material containment vessel is configured to dispense a quantity of material and supported on the receiver end such that a portion of the vessel is secured to the body portion and another portion of the vessel is moveable relative to the body portion. In one aspect of the invention, the material containment vessel is a syringe. The actuator has a first end connected to the actuator drivetrain and a second end configured to connect to and support the moveable portion of the vessel in both of a dispensing movement that exerts pressure on the material and a retracting movement that relieves pressure applied to the material. The control unit receives actuator parameter inputs and includes a sensor to detect a signal of at least one of a pressure level and a time period. The sensor provides the detected signal to the control unit such that the control unit operates the actuator between the dispensing and retracting movements based on the detected signal and the actuator parameter inputs.

The invention further relates to a method of controlling an actuator for dispensing a bone graft substitute material that includes the steps of initiating a dispensing cycle, comparing measured values of pressure and time to predetermined threshold levels, determining a state of material delivery based on the comparison, and controlling operation of the actuator in response to the determined state of material delivery.

Various aspects of this invention will become apparent to those skilled in the art from the following detailed description of the preferred embodiment, when read in light of the accompanying drawings.

DETAILED DESCRIPTION OF THE PREFERRED EMBODIMENT

Figure 1:
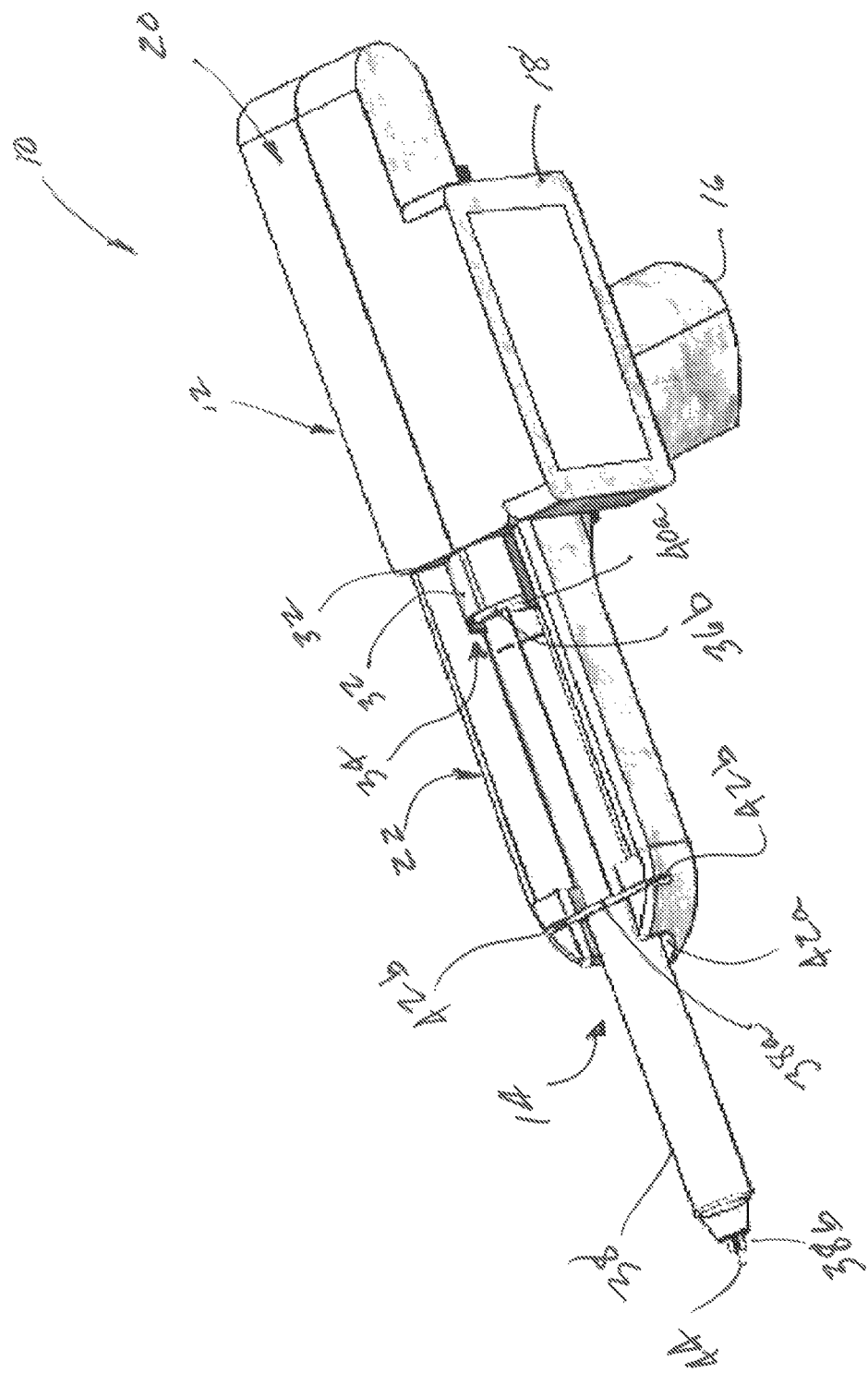
FIG. 1 is a perspective view of an apparatus for injecting bone graft substitute and other materials in accordance with this invention.
Figure 2:
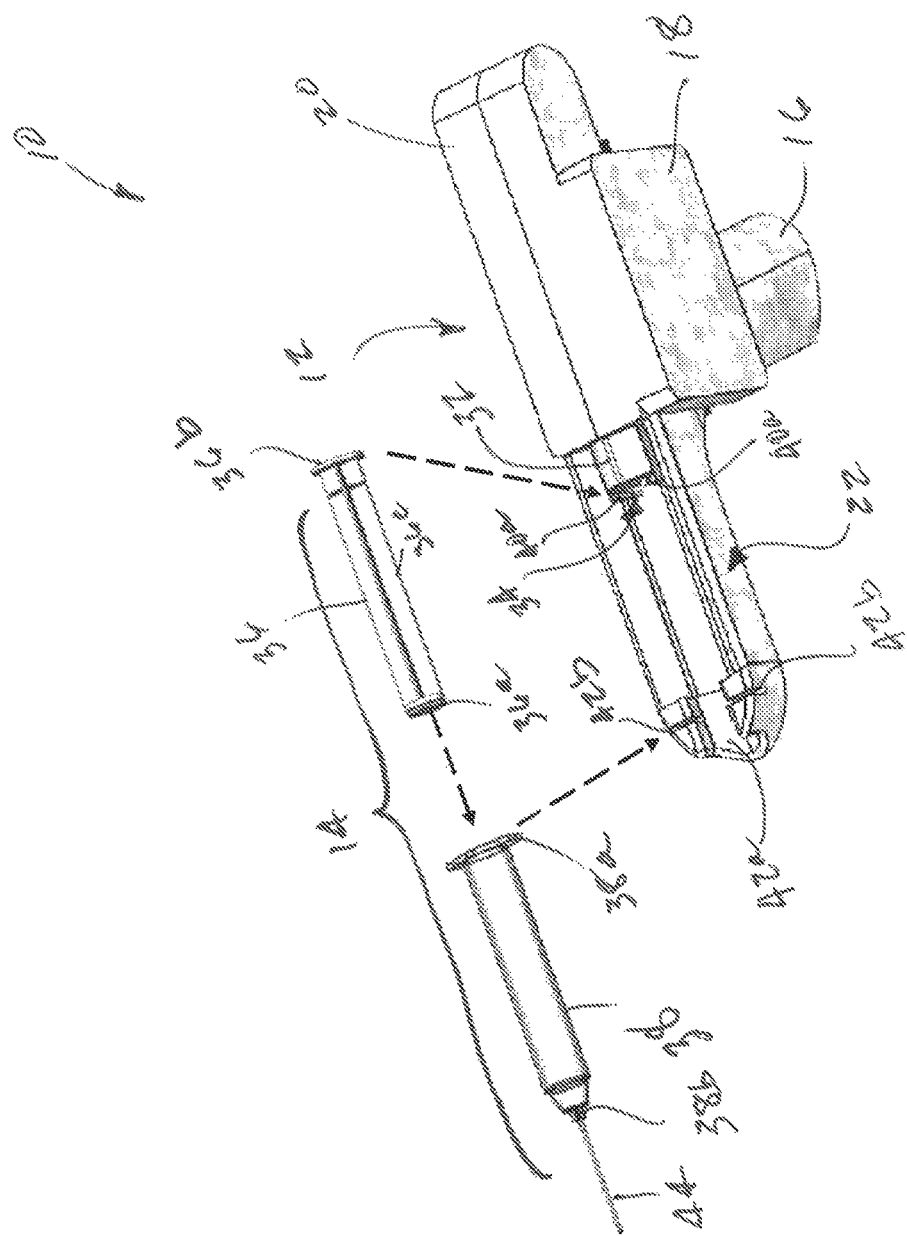
FIG. 2 is an exploded perspective view of the apparatus for injecting bone graft substitute and other materials illustrated in FIG. 1.
Figure 3:
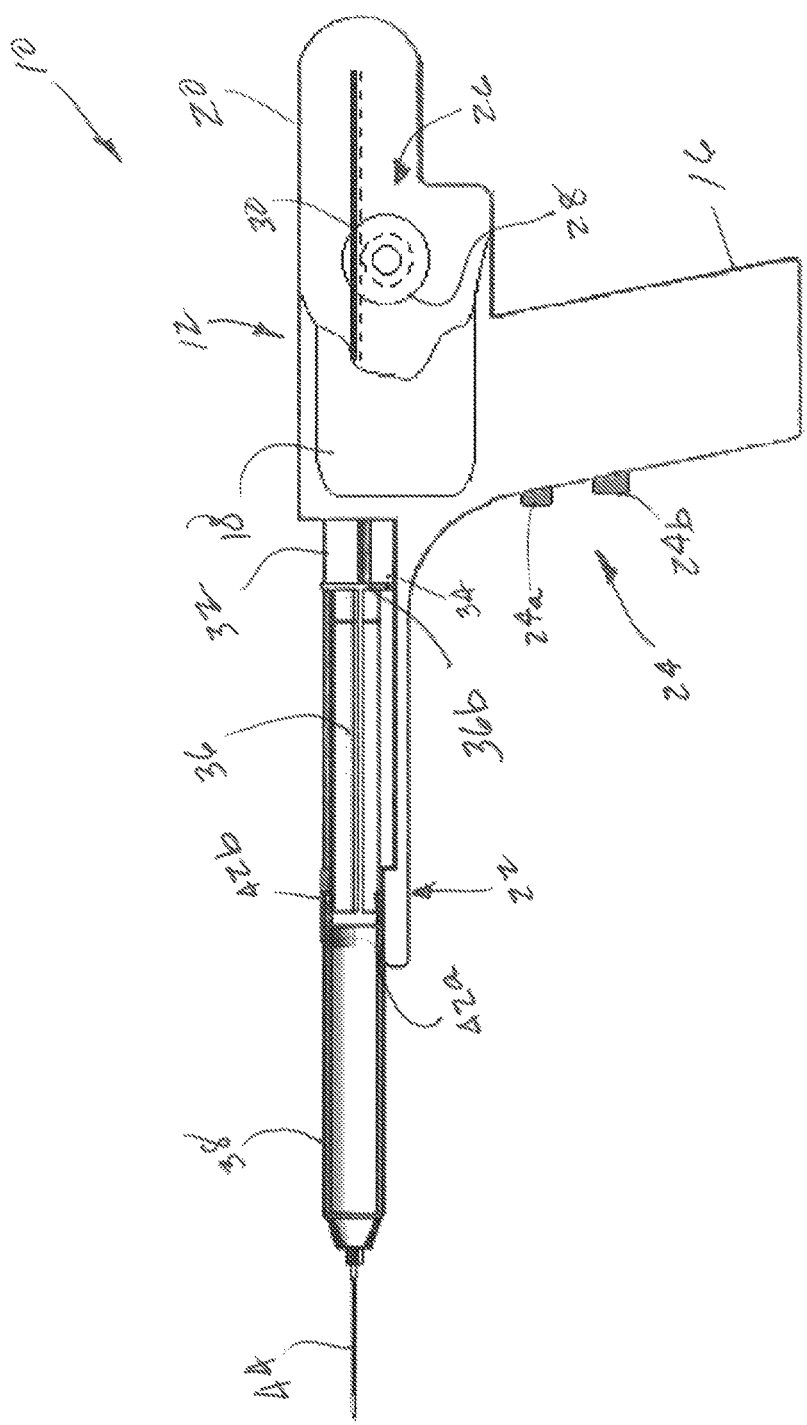
FIG. 3 is a side elevational view, partially broken away, of the apparatus for injecting bone graft substitute and other materials illustrated in FIGS. 1 and 2.

Referring now to the drawings, FIGS. 1-3 illustrate an embodiment of a metering delivery apparatus, indicated generally at 10, for injecting bone graft substitute and other materials in accordance with this invention. The metering delivery apparatus 10 includes a body portion, shown generally at 12, and a material containment vessel, shown generally at 14. In one embodiment, the body portion 12 is illustrated as having a shape suitable for hand-held use and further having a general pistol shape, though other shapes, such as for example a wand-like shape similar to a flashlight, may be used and still remain within the scope of the invention. Alternatively, the body portion may be divided between a stationary portion and a hand-held portion. The body 12 includes a hand grip 16, a display/input screen 18, a drive housing 20 and a receiver end 22. The hand grip 16, as shown in FIG. 3, extends from the body portion 12 and supports a forward/reverse switch 24, illustrated as two buttons 24a and 24b. The switch 24 may alternatively be configured as any input switch, such as a toggle switch, trigger switch, or adjustable potentiometer capable to power the device in a dispense and retract condition, as will be explained below. The hand grip 16 may be a hollow structure forming a circuit housing to conceal and support various integrated circuit boards that control operation of the apparatus 10, as will be explained below. In addition, the hand grip 16 may contain a battery pack (not shown) to power the device.

The display/input screen 18 is illustrated as supported by or mounted on the body portion 12, though the screen 18 may be a separate component that connects via a wire connection or wirelessly. In one embodiment, the screen 18 is a display and touch screen capable of accepting programming inputs to adjust operation parameters and display sensor and performance information. The screen 18, however, may be configured as a display having any type of input configuration, such as preprogrammed or user-defined buttons, USB ports for input from a laptop or phone, or other wireless connections, such as a Blue Tooth connection. The drive housing 20 is configured to orient and support a drive assembly, shown generally at 26 in FIG. 3. The drive assembly 26 includes a motor 28 and a drivetrain 30. In one embodiment, the drivetrain 30 may be a mechanical, geared drive having a rack and pinion gear set, planetary gear set, worm and sector drive, or screw thread drive. A portion of the drivetrain 30 is connected to an actuator 32. The actuator 32 is configured to be driven between an extended position, that deploys the contents of the material containment vessel 14, and a retracted position, that relieves pressure exerted on the contents of the material containment vessel 14 to stop flow of the material. Alternatively, the motor 28 may power a hydraulic pump connected to a piston that drives the actuator 32.

The actuator 32 includes a mounting end 34 that is configured to engage a portion of the material containment vessel 14. In the illustrated embodiment, the vessel 14 is shown as a syringe having a plunger 36 and a barrel 38. The plunger 36 includes a tip 36a that forms a seal against inner surfaces of the barrel 38 and a flanged end 36b. In the illustrated embodiment, the flanged end 36b is larger than a shaft portion 36c that extends between it and the tip 36. The mounting end 34 of the actuator 32 includes a connection point 40 that is configured to secure the flanged end 36b to the actuator such that extension and retraction movement of the actuator 32 is transferred to the plunger 36. In the specific embodiment, the connection point 40 is illustrated as hooks or slots 40a that extend around a portion of the flanged end 36b. The receiver end 22 extends from the drive housing 20 of the body 12. The receiver end 22 terminates in a cradle 42a and slots 42b that extend generally perpendicularly from the cradle 42a. The cradle 42a supports the barrel 38 and the slots accept a flanged end 38a to restrict movement of the barrel 38 relative to the plunger 36. The barrel 38 terminates in a hub 38b that accepts a needle 44 or other tubing or other device to deliver the contents of the material containment vessel 14 to the intended site, specifically bone cement (bone graft substitute) to the affected boney structure in the patient. The cradle 42a and slots 42b, in conjunction with the mounting end 34 of the actuator 32, permits the syringe 14 to be installed into the receiver end 22. Typically, the syringe 14 is in an extended position and filled with bone cement, and the actuator 32 is retracted sufficiently to permit the extended syringe to drop into place—engagement with the cradle 42a, slots 42b, and the mounting end 34. In one embodiment, the barrel flange 38a and the plunger flange 36b snap fit into the respective slots. In an alternative embodiment, the flanges 38a and 36b form a slip fit with the respective slots.

Figure 4:
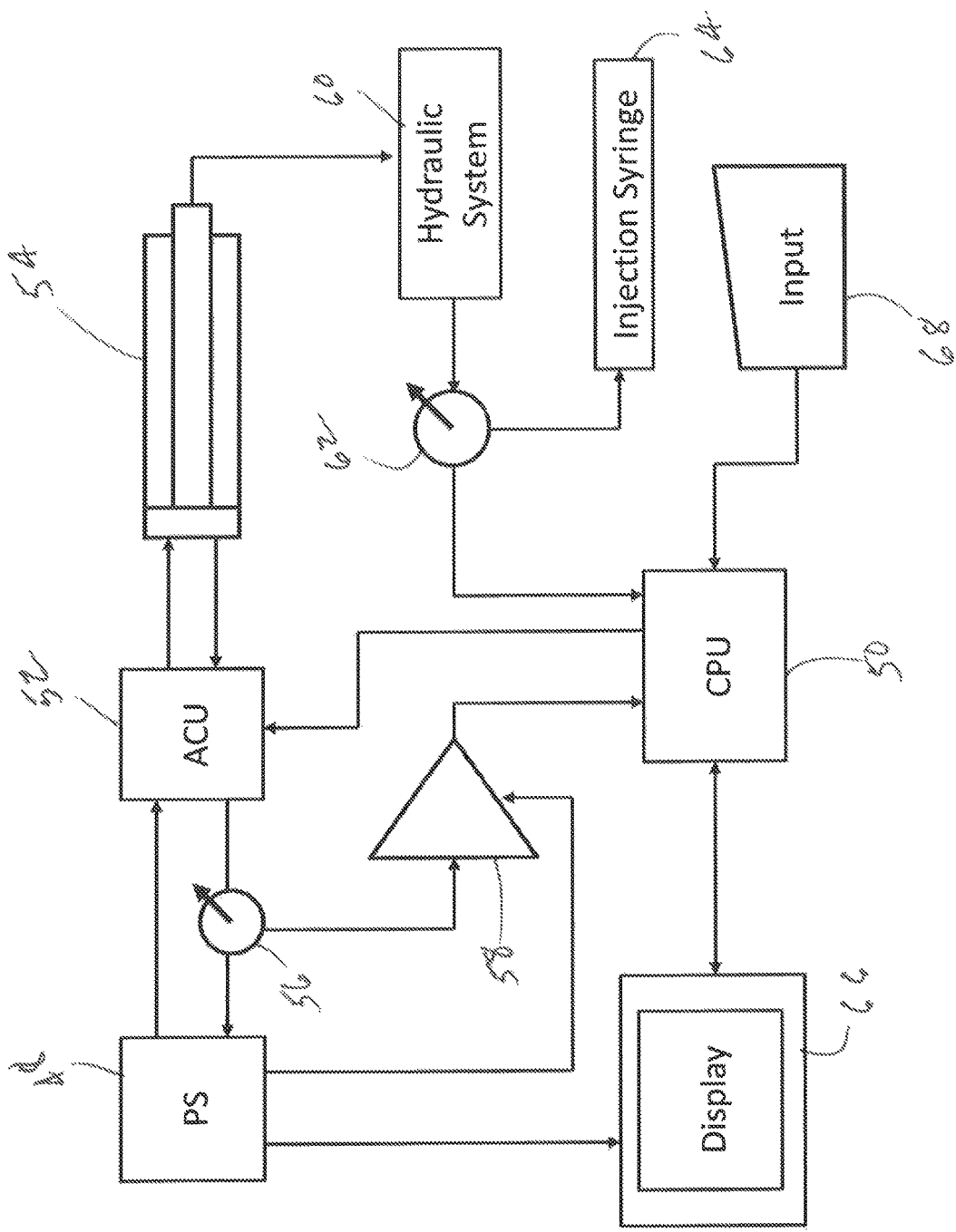
FIG. 4 is a block diagram of the components of the apparatus for injecting bone graft substitute and other materials illustrated in FIGS. 1 through 3.

Referring now to FIG. 4, there is illustrated a block diagram of the components of the apparatus for injecting bone graft substitute and other materials, as illustrated in FIGS. 1-3. These components generally can include a power supply 48, a central processing unit/micro-controller (CPU) 50, an actuator control unit 52, a linear actuator 54, a current sensing device 56, a low-loss, single supply amplification circuit 58, a hydraulic force transfer system 60, a pressure sensor 62, a syringe of inject-able material 64, a display system 66, and a human interface control unit 68. The power supply 48 provides the desired voltage and current necessary for operation of the other components. The central processing unit 50 performs calculations used by the system and contains the software which controls the actuator and display. In one embodiment, the actuator control unit 52 takes the low current/voltage signals from the CPU 50 and uses these signals to control higher current sources used by the actuator to provide both forward and reverse motion. The linear actuator 54 converts the electrical energy into mechanical energy and is used to power the hydraulic system 60. In this embodiment, the hydraulic system 60 is used either in conjunction with or in place of the mechanical drivetrain 30.

Current used to power the actuator passes through the current sensing device 56 which outputs a voltage signal based on the power consumed by the actuator 54. The voltage signal passes through a high precision single supply amplifier 58 and is converted to a digital signal by either the CPU 50 or an analog-digital converter. The CPU 50 uses the digital signal to calculate the pressure within the injection syringe 64. The current sensor 56 and amplifier 58 can either be used with or in place of the pressure sensor 62. Hydraulics 60 are used to increase the force the system is able to produce to allow for higher injection pressures. The hydraulic system 60 is an optional component and can be omitted in favor of a higher force producing linear actuator, as described above. Pressure within the hydraulic system 60 can be measured through the use of a pressure sensor 62 measuring the pressure within the working fluids of the hydraulic system. Alternatively, in embodiments with a linear actuator or mechanical drive assembly, a load sensor or strain gage may be substituted for the pressure sensor 62 to provide the similar functionality of sensing forces imparted by the actuator 32 and the system resistance to movement. The CPU 50 uses the pressure measurement to calculate the pressure within the injection syringe 64. The pressure sensor 62 can be used in conjunction with or in lieu of the current sensing method of determining injection pressure. The syringe 64 at the end of the hydraulic system 60 contains the fluid, such as bone graft substitute, that is to be injected.

An optional display unit 66 can be used to display the injection pressure to the user as well as any other pertinent information. As described above, the display unit 66 may also be a touch screen allow for controlling settings within the CPU 50. In a second embodiment, the human interface component 68 of the system contains a forward/reverse switch as well as a button to initiate the injection process. When the injection button is depressed, the injection syringe 64 will either expel or take in material depending on the position of the forward/reverse switch and the state of the CPU 50. The power supply 48 can be of any suitable design to provide the linear actuator 54 with the current necessary for operation and provides the rated voltages for the actuator control unit 52, CPU 50, single supply amplifier 58, and the display 66. If a micro-controller is used in place of a standard processor or field-programmable gate array (FPGA), voltages may be produced by way of voltage regulators within the micro-controller 50. The power supply 48 can use the US standard electrical outlets as its source or rechargeable or disposable batteries. When using the 120 VAC 60 Hz electricity, it may be desired to use a transformer (not shown) to scale the voltage and provide isolation from power fluctuations that may be present in the electrical lines. A full wave rectifier may also be used to invert any negative voltages relative to ground. A smoothing circuit composed of a Zener diode and capacitor in parallel may also be used after the rectifier to provide a smooth DC voltage. Since many components use different voltages, in one embodiment it may be desirable to have the output voltage of the smoothing circuit at the highest required voltage and use voltage regulators to obtain the smaller voltages that may be needed.

In certain embodiments, it may be desired that rechargeable or disposable batteries be used to power the automated injection system 10. Using a battery powered source provides the ability of creating a portable or hand-held injection system. In another embodiment, multiple batteries may be used in parallel, in conjunction with diodes to prevent back-feeding of the batteries. Voltage regulators can then be used to obtain the desired voltages from multi-battery power source, which further provides a more tightly regulated power supply.

The CPU 50 is composed of the circuitry and software which regulates and controls the automated injection system. The CPU 50 can be implemented through the use of a micro-controller, field programmable gate array, personal computer, or other types of processors. Regardless of the type of implementation, the CPU 50 receives inputs from the user through the input interface 68, such as the initiate button and the forward/reverse switch, and also receives input from the current sensor 56 or the direct pressure sensor 62. The analog signal from the current sensor 56 and pressure sensor 62 are converted to digital signals through either discrete analog to digital converters or through circuitry already built into the CPU 50. (Depending on the type of display used inputs may also be received through the touch screen). The digital signal received from the current sensor 56 may be used to calculate the power used by the linear actuator 54. This current value can then be compared to a calibration curve and used to calculate the pressure within the injection syringe 64. Similarly the signal from the pressure sensor 62 may be compared to its own calibration curve to determine the injection syringe pressure. The CPU 50 outputs the calculated pressure from either sensor to the display screen 66 so the user can be alerted to the injection pressure.

Figure 5:
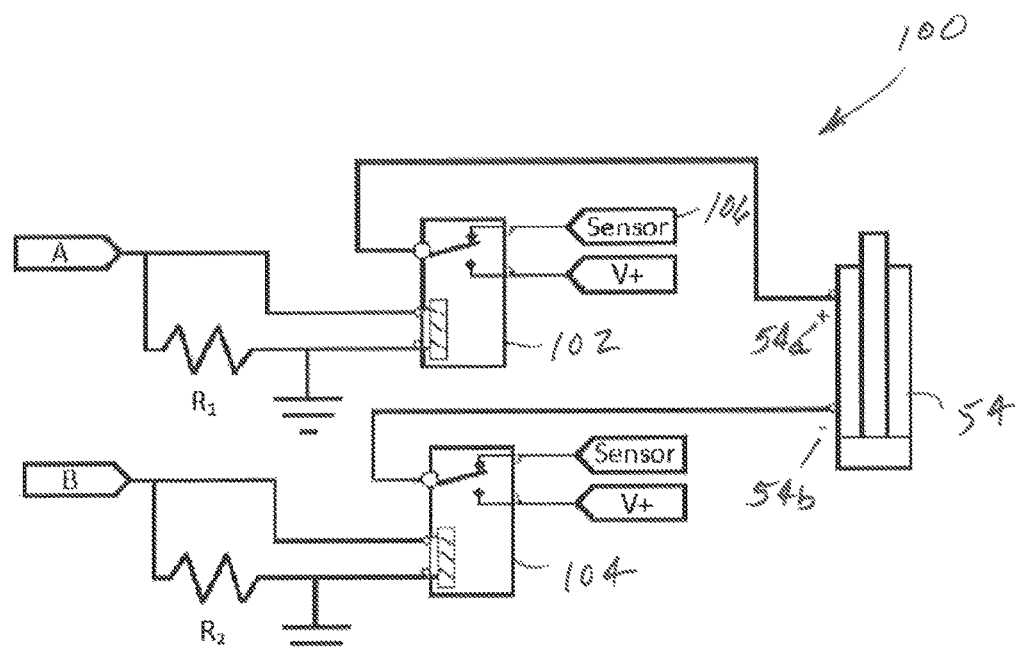
FIG. 5 is a schematic diagram of a first embodiment of a circuit for controlling the direction of movement of the linear actuator illustrated in FIG. 4.

FIG. 5 is a schematic diagram of a first embodiment of a control circuit, shown generally at 100, for controlling the direction of movement of the linear actuator 54, illustrated in FIG. 4. The control circuit 100 uses two single pole, double throw relays 102 and 104 to expose the positive and negative terminals 54a and 54b, respectively, of the actuator 54 to either its voltage source or ground. If the system uses the current sensing method to calculate the injection pressure, the control circuit 100 will first direct the current through the current sensor before it connects to ground. The voltage signals at signal points A and B are controlled by the CPU 50 and are used to turn the relays on and off. These signals are connected to ground via the pull down resistors R1 and R2 to ensure that the relays 102 and 104 are deactivated when the voltage signals are not in a high state. The high state voltage to turn on the relays is determined by the manufacturer of the relays. When the relay 102 controlled by signal A is energized, it will connect the positive terminal of the actuator to its voltage source, and when it is de-energized, the positive terminal will be connected to either ground or a current sensor 106, similar to current sensor 56 described above. Similarly, the relay 104 controlled by signal B will connect the negative terminal of the actuator 54 to either the voltage source or the current sensor/ground depending on whether the relay 104 is turned on or off. The actuator 54 will create a forward or dispensing motion when signal A is high and B is low and reverse motion when signal A is low and B is high. The actuator 54 will not consume power and will be idle if signal A and B are both high or both low.

Figure 6:
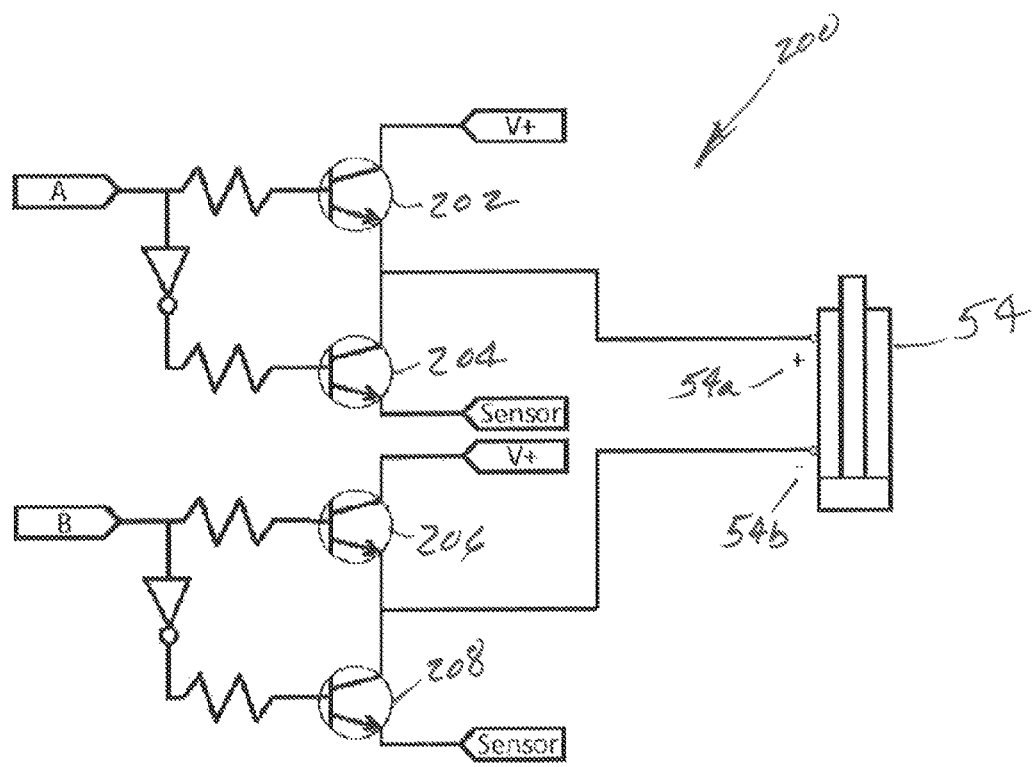
FIG. 6 is a schematic diagram of a second embodiment of a circuit for controlling the direction of movement of the linear actuator illustrated in FIG. 4.

FIG. 6 is a schematic diagram of a second embodiment of a circuit, shown generally at 200, for controlling the direction of movement of the linear actuator illustrated in FIG. 4. The control circuit 200 operates similarly to the control circuit 100, however the relays 102, 104 are replaced by transistors 202, 204, 206, and 208 to control the connections of the voltage source or the current sensor/ground to the positive and negative terminals 54a and 54b of the actuator 54. In a similar manner, the control circuit 200 controls power supply to the actuator to create forward motion when signal A is high and B is low, and reverse motion when signal A is low and B is high. The control circuit 200 generally will not consume power and will be idle if signal A and B are both high or both low. This method provides the advantage of allowing for a smoother transition between stopping and running the actuator, thus reducing vibrations or jerking motions resulting from sudden activation of the actuator. Depending on current required to power the actuator, the transistors 202, 204, 206, and 208 may include one or more heat sinks to control high amounts of heat generated during use.

Figure 7:
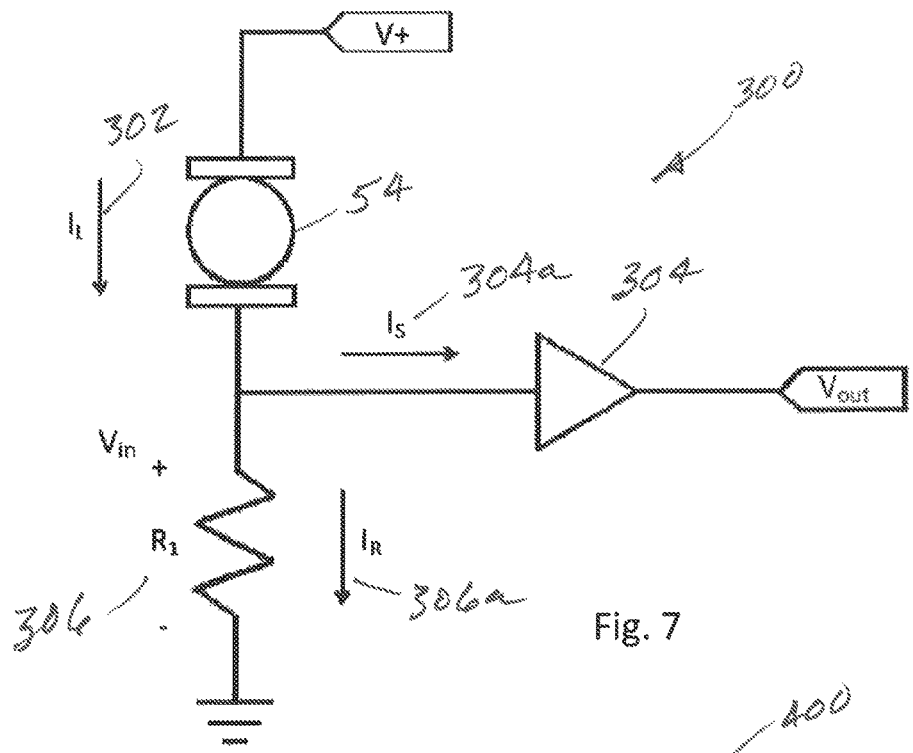
FIG. 7 is a schematic diagram of a current sensor circuit for determining the power consumed by the actuator illustrated in FIG. 4.

FIG. 7 is a schematic diagram of a current sensor circuit, shown generally at 300, which may be used to determine the power consumed by the actuator 54. The current sensor circuit 300 is configured to measure the current flowing through the actuator 54. The resulting value of current flowing through the actuator 54 may be transmitted to the CPU 50. In one embodiment, software code resident in the CPU 50 applies Ohm's Law to calculate the power using the equation $P=i*V$ where i is the current flowing through the actuator and V is the voltage drop across the actuator. From Kirchhoff's Current Law, the sum of the current entering a node is equal to the current leaving the node. In the embodiment of the current sensor circuit 300, current 302 passing through the actuator 54 is generally equal to the sum of current 304a passing through an amplifier 304 and current 306a passing through a resistor 306. Since the amplifier 304 has a theoretical infinite resistance, the software is programmed to assumed that no current flows through the amplifier circuit branch. Thus, the current flowing through the actuator 54 is equal to the current flowing through the resistor 306. The software code then applies Ohm's law to determine the current through the resistor and thus the actuator. The current 302 is determined by dividing the voltage drop across the resistor 306 by the known value of the resistor 306. To provide a large voltage drop across the actuator 54, the voltage drop across the resistor 306 will be small. The resistor 306 will exhibit a very small resistance value. When using a small resistance value for resistor 306, an amplifier circuit, such as amplifier circuit 400 of FIG. 8, may be used to increase the voltage signal to a value that can be more accurately and easily measured by the CPU 50. The CPU 50 can calculate the actual voltage drop across the resistor 306 based on the measured voltage in conjunction with the amplifier circuit. The power consumed by the actuator 54 is then calculated by multiplying the voltage drop across the actuator 54 by the current through the resistor 306. Generally, the voltage drop across the actuator 54 is equal to the value of the voltage source minus the voltage drop across the resistor. The current through the resistor 306 is equal to the voltage drop across the resistor 306 divided by the resistance value. Thus, in one embodiment, the software code utilizes $P=(Vs-Vin)*Vin/R$ to calculate the power consumed by the actuator 54.

Figure 8:
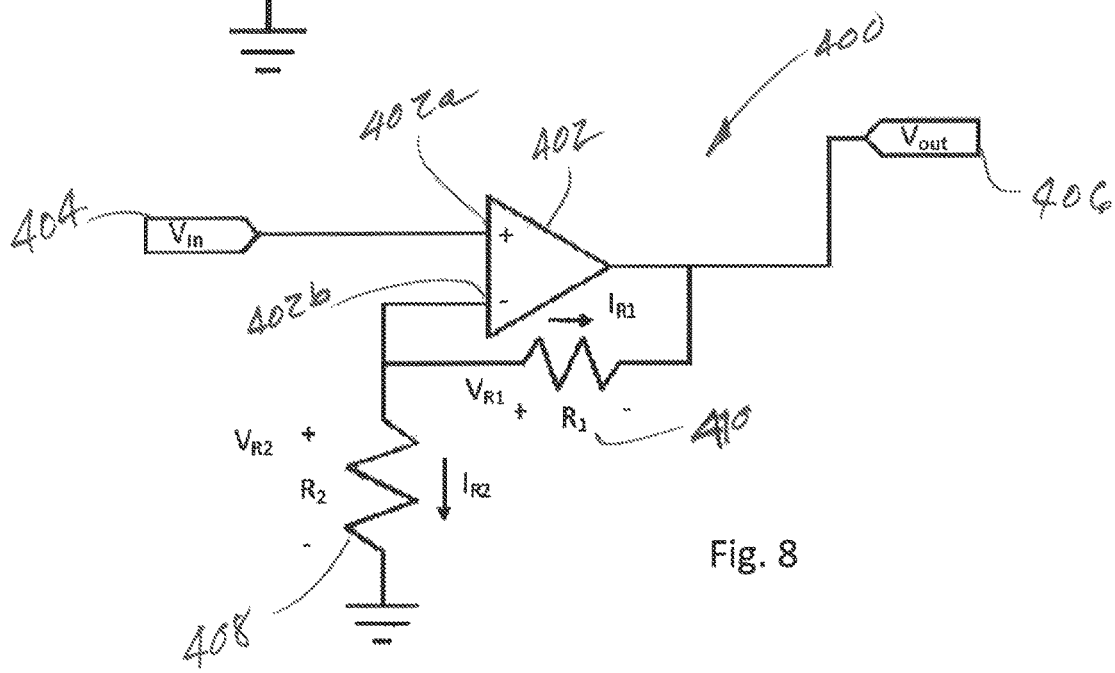
FIG. 8 is a schematic diagram of the amplification circuit illustrated in FIG. 4.

FIG. 8 is a schematic diagram of an amplification circuit, shown generally at 400 and functionally similar to the amplifier 58 illustrated in FIG. 4. In one embodiment, the amplifier circuit 400 includes an amplifier 402 that may be configured as a high precision, single supply, rail to rail amplifier. In this configuration, amplifier 402 provides increased measurement accuracy and permits a more precise indication of the pressure within the injection syringe 64. Amplifier 402 linearly increases an input voltage, Vin, 404 to a higher value output voltage, Vout 406, when the input voltage 404 is applied to the non-inverting input 402a. For amplifier 402, the resistance between the non-inverting input 402a and an inverting input 402b is considered infinite, thus the current between inputs 402a and 402b is taken as 0 amps. The voltage $V_{R2}$ across resistor (R2) 408 is equal to Vin, and the voltage $V_{R1}$ across resistor (R1) 410 is equal to Vin−Vout. Using Ohm's Law, the current through R1 410 can be calculated as Vin−Vout divided by the value of resistor (R1) 410. The current through resistor (R2) 408 can be calculated as Vin divided by the resistance of R2 408. Using Kirchhoff's Current Law, the current through the amplifier 402, which may be assumed to be zero, plus the current through R1 410 plus the current through R2 408 is equal to zero. The non-inverting amplification voltage may be characterized by the equation Vout=(R1/R2+1)*Vin. The CPU 50 can measure the value of Vout 406 with a high degree of accuracy. Vin and subsequently the power consumed by the actuator can be determined. The power consumed by the actuator 54 can be compared to a standard curve or look-up table for a particular actuator to determine the pressure within the injection syringe 64.

Figure 9:
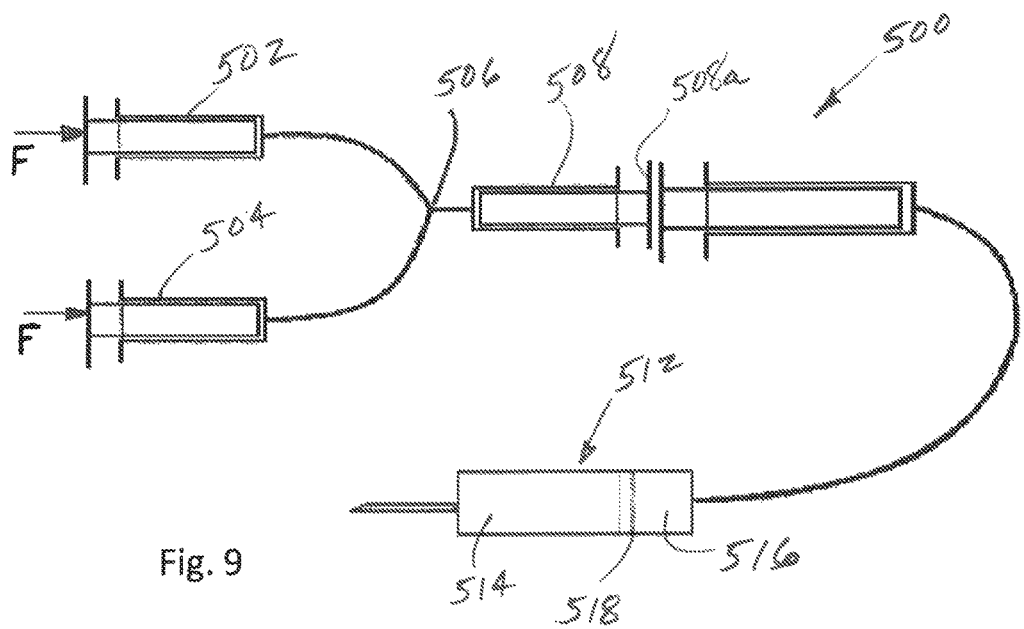
FIG. 9 is a schematic diagram of a hydraulic system for operating the linear actuator illustrated in FIG. 4.

FIG. 9 is a schematic diagram of an embodiment of a hydraulic system, shown generally at 500, for operating the linear actuator 54 illustrated in FIG. 4. The actuator 54 applies a force F to hydraulic cylinder/piston assemblies 502 and 504, which are illustrated in a particular embodiment as syringes, though such a configuration is not required. The fluid within the syringes 502 and 504 come together at a manifold junction 506(3) and enters a third hydraulic cylinder/piston assembly 508, also illustrated as a syringe. If syringes 502, 504, and 508 are of the same cross sectional area the force at the output of syringe 508, at a flanged end of plunger 508a, will be double the force, F applied by the actuator 54. The cross sectional area of syringes 502 and 504 can be increased to further increase the force amplification. This output force from syringe 508 is transferred to a hydraulic cylinder/piston assembly 510, also illustrated as a syringe, with a larger cross sectional area. The fluid from syringe 510 is used to operate a dual chambered cylinder/piston assembly, shown as syringe 512. The syringe 512 defines a distal chamber 514 and a proximal chamber 516 separated by a piston 518. The distal chamber 514 of the dual chamber syringe 512 is also known as an injection syringe and contains the material to be injected. In one embodiment, the syringe 512 has a relatively smaller cross sectional area further increasing the force applied to the contents of the distal chamber 514.

As stated above, hydraulic systems, such as hydraulic system 500, is an optional component of the metering delivery apparatus 10. In certain embodiments, the hydraulic system 500 allows for the use of a less powerful actuator by creating a higher injection pressure with a smaller input force from the actuator 54. The CPU 50 implements a method, as will be described below in detail, which is based in part on Pascal's Law, along with certain operational assumptions. Pascal's Law states that in a closed system a change in pressure will be transmitted without loss to the rest of the system. Since the hydraulic system will be relatively level or momentary attitudes of the fluid systems during use will have little impact on the overall operation, in one embodiment the software can assume no change in height such that the pressure at any two points in the system can be assumed to be constant. Thus, the force at any point in the system divided by its cross sectional area will remain generally constant. Therefore, a pressure sensor, such as pressure sensor 62, can be attached to any point of the hydraulic system and the CPU 50 can use the signal from the sensor to determine the pressure within the injection syringe.

Figure 10:
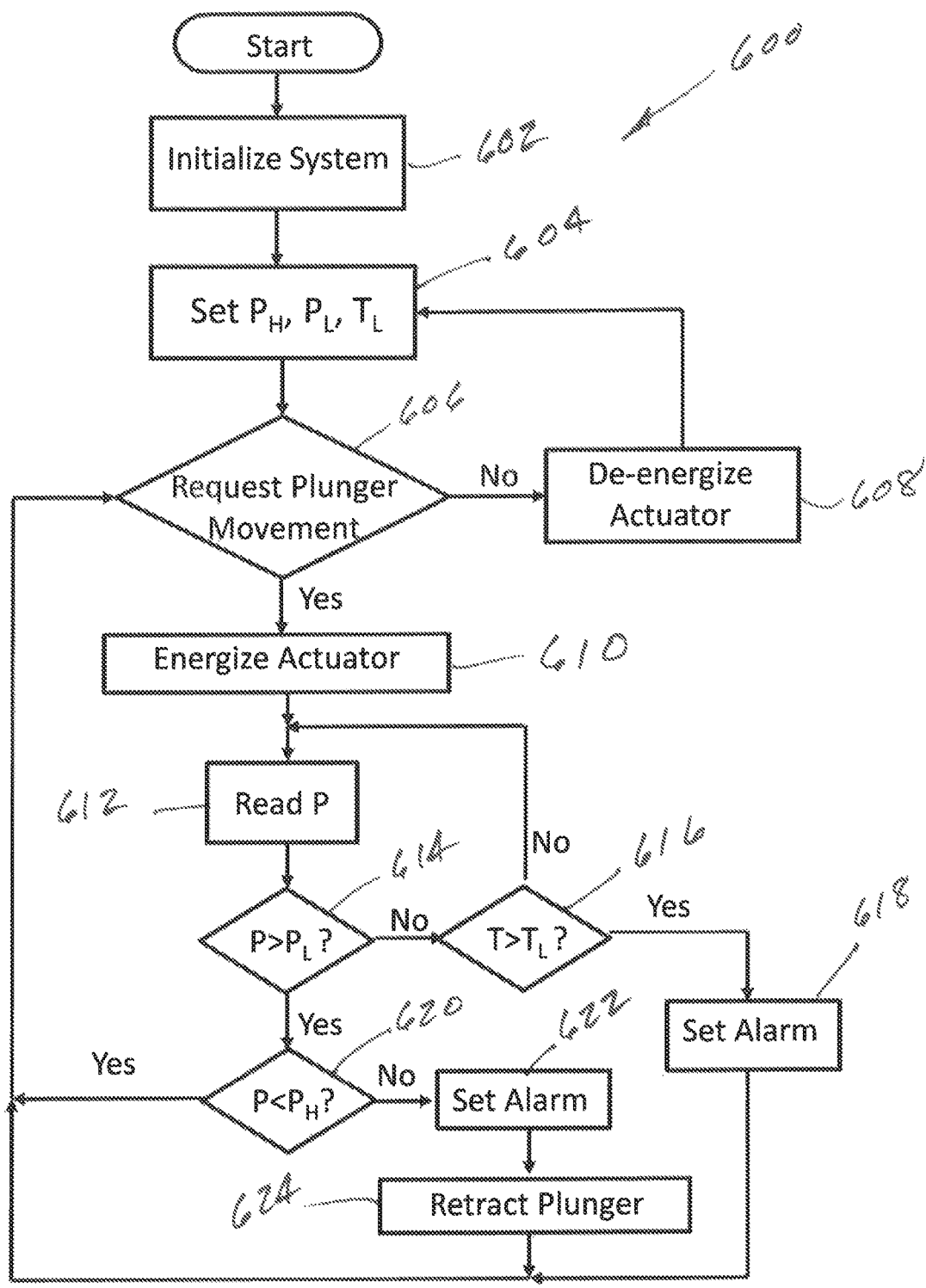
FIG. 10 is a flowchart of a method for operating the apparatus for injecting bone graft substitute and other materials in accordance with this invention.

FIG. 10 is a flowchart of a method, indicated generally at 600, for operating the apparatus 10 of FIG. 1 for injecting bone graft substitute and other materials in accordance with this invention. The method 600 begins with an initial instruction 602, wherein one or more parameters of the apparatus 10 for injecting bone graft substitute are initialized in a conventional manner. Then, the method 600 enters another instruction 604, wherein the values of certain parameters used in the performance of this method 600 are set. In the illustrated embodiment, the values of three of such parameters $P_H$, $P_L$, and $T_L$ are set. The parameter $P_H$ is representative of an upper pressure limit that is expected during normal use of the apparatus 10 for injecting bone graft substitute. The parameter $P_L$ is representative of a lower pressure limit that is expected during normal use of the apparatus 10 for injecting bone graft substitute. The parameter $T_L$ is representative of an amount of time that is expected to be needed for the pressure of such bone graft substitute to achieve the lower pressure limit $P_L$ during a normal initial commencement of use of the apparatus 10 for injecting bone graft substitute. Although this method 600 will be described in the context of the illustrated three parameters $P_H$, $P_L$, and $T_L$, it will be appreciated that a greater or lesser number of such parameters (and other parameters) may be used.

Following this initialization, the method next enters a decision point 606, wherein it is determined whether a request has been made to move the plunger 36 relative to the syringe barrel 38. As discussed above, a request to move the plunger 36 may, for example, be made by depressing one of the buttons 24a and 24b provided on the handle 16 of the actuator body 12. If no request has been made to move the plunger 36 relative to the syringe barrel 38, then the method 600 branches from the decision point 606 to an instruction 608, wherein the actuator 608 is de-energized (or, if already de-energized, caused to remain de-energized). Then, the method 600 returns to the parameter input step 604 which may then automatically cycle to decision point 606 (if no changes are made to the parameters), wherein it is again determined whether a request has been made to move the plunger 36 relative to the syringe barrel 38. The method 600 cycles through this loop until it is determined that a request has been made to move the plunger 36 relative to the syringe barrel 38.

When it is determined, however, that a request has been made to move the plunger 36 relative to the syringe barrel 38, the method 600 branches from the decision point 606 to an instruction 610, wherein the actuator 54 is energized. As a result, the plunger 36 is moved relative to the syringe barrel 38 in the manner described above. Such movement of the plunger 36 relative to the syringe barrel 38 causes the pressure of the bone graft substitute being injected from the syringe barrel 38 to increase.

The method 600 next enters an instruction 612, wherein the magnitude of the pressure P of the bone graft substitute being injected from the syringe barrel 38 is determined. The determination of this pressure P can be made in any desired manner. For example, the determination of the pressure P can be made by means of a conventional sensor (not shown)

that makes a direct measurement thereof. Alternatively, the determination of the pressure P can be made indirectly, such as by a conventional mathematical algorithm that is based upon the value of one or more operating parameters, such length and velocity of the movement of the plunger 36 relative to the syringe barrel 38, the area of the plunger 36 and the syringe barrel 38, the viscosity of the bone graft substitute being injected from the syringe barrel 38, and the like.

The method 600 next enters a decision point 614, wherein the magnitude of the pressure P of the bone graft substitute being injected from the syringe barrel 38 is compared with the parameter $P_L$. As described above, the parameter $P_L$ is representative of a lower pressure limit that is expected during normal use of the apparatus 10 for injecting bone graft substitute. Prior to the initial use of the apparatus 10 for injecting bone graft substitute, the magnitude of the pressure P of the bone graft substitute being injected will initially be zero. Thus, when use of the apparatus 10 initially begins, it is expected that the magnitude of the pressure P of the bone graft substitute being injected will rise from zero toward the lower pressure limit $P_L$.

If, in the decision point 614, it is determined that the magnitude of the pressure P of the bone graft substitute is not greater than the parameter $P_L$, then the method 600 branches from the decision point 614 to a decision point 616, wherein an elapsed time parameter T (which can be defined as the amount of time that has elapsed since the actuator 54 was energized) is compared with the parameter $T_L$. As also described above, the parameter $T_L$ is representative of an amount of time that is expected to be needed for the pressure of such bone graft substitute to achieve the lower pressure limit $P_L$ during a normal initial commencement of use of the apparatus 10 for injecting bone graft substitute. If the elapsed time T is not greater than the parameter $T_L$, then the method 600 branches from the decision point 616 back to the instruction 612, wherein the magnitude of the pressure P of the bone graft substitute being injected from the syringe barrel 38 is again determined. This loop of the method 600 is repeated until either (1) in the decision point 614, it is determined that the pressure P of the bone graft substitute is greater than the parameter $P_L$, or (2) in the decision point 616, it is determined that the elapsed time T is greater than the parameter $T_L$.

If the latter event occurs first (i.e., it is determined in the decision point 616 that the elapsed time T is greater than the parameter $T_L$), then the amount of time that is expected to be needed for the pressure of the bone graft substitute to achieve the lower pressure limit $P_L$ has been exceeded. Accordingly, it can be inferred that a fault has occurred in the apparatus 10 for injecting bone graft substitute, such as a defective actuator or a leak in a line extending from the syringe barrel 38, for example. Regardless, when this latter event occurs, the method 600 branches from the decision point 616 to an instruction 618, wherein an alarm is generated. The alarm may be generated in any desired manner (such as visual, audible, tactile, for example) and may, if desired, include automatically de-energizing the actuator 54.

If, on the other hand, the former event occurs first (i.e., it is determined in the decision point 614 that the magnitude of the pressure P of the bone graft substitute is greater than the parameter $P_L$, then the method 600 branches from the decision point 614 to a decision point 620, wherein the magnitude of the pressure P of the bone graft substitute being injected from the syringe barrel 38 is compared with the parameter $P_H$. As described above, the parameter $P_H$ is representative of an upper pressure limit that is expected during normal use of the apparatus 10 for injecting bone graft substitute. If, in the decision point 620, it is determined that the magnitude of the pressure P of the bone graft substitute is less than the parameter $P_H$, then the method 600 branches from the decision point 620 back to the decision point 606, wherein it is determined whether a request has been made to move the plunger 36 relative to the syringe barrel 38, such as by depressing one of the buttons 24a or 24b provided on the handle 16 as described above.

However, if, in the decision point 620, it is determined that the pressure P of the bone graft substitute is not less than the parameter $P_H$, then the method X00 branches from the decision point 620 to an instruction 622, wherein an alarm is generated. The alarm may be generated in any desired manner (such as visual, audible, tactile, for example) and may, if desired, include automatically de-energizing the actuator 54. Then, the method enters another instruction 624, wherein the plunger 36 is caused to retract within the syringe barrel 38 effectively reducing the system pressure P.

Thus, it can be seen that the method 600 of this invention monitors the magnitude of the pressure P of the bone graft substitute being injected from the syringe barrel 38. After the lower pressure limit $P_L$ that is expected during normal use of the apparatus 10 has been initially achieved as described above, the method 600 of this invention repeatedly compares the magnitude of the pressure P of the bone graft substitute being injected from the syringe barrel 38 with both the upper pressure limit $P_H$ and the lower pressure limit $P_L$. If the magnitude of the pressure P of the bone graft substitute rises above the upper pressure limit $P_H$, then it can it can be inferred that a fault has occurred in the apparatus 10 for injecting bone graft substitute, such as blockage in a part of the system, such as any line extending from the syringe barrel 38, or the cavity being supplied with the bone graft substitute has become filled. Alternatively, if the magnitude of the pressure P of the bone graft substitute rises falls below the lower pressure limit $P_H$, then it can also be inferred that a fault has occurred in the apparatus 10 for injecting bone graft substitute, such as a defective actuator or a leak in a line extending from the syringe barrel 38. In either event, the method 600 of this invention automatically generates an alarm and takes other action as deemed appropriate.

Figure 11:
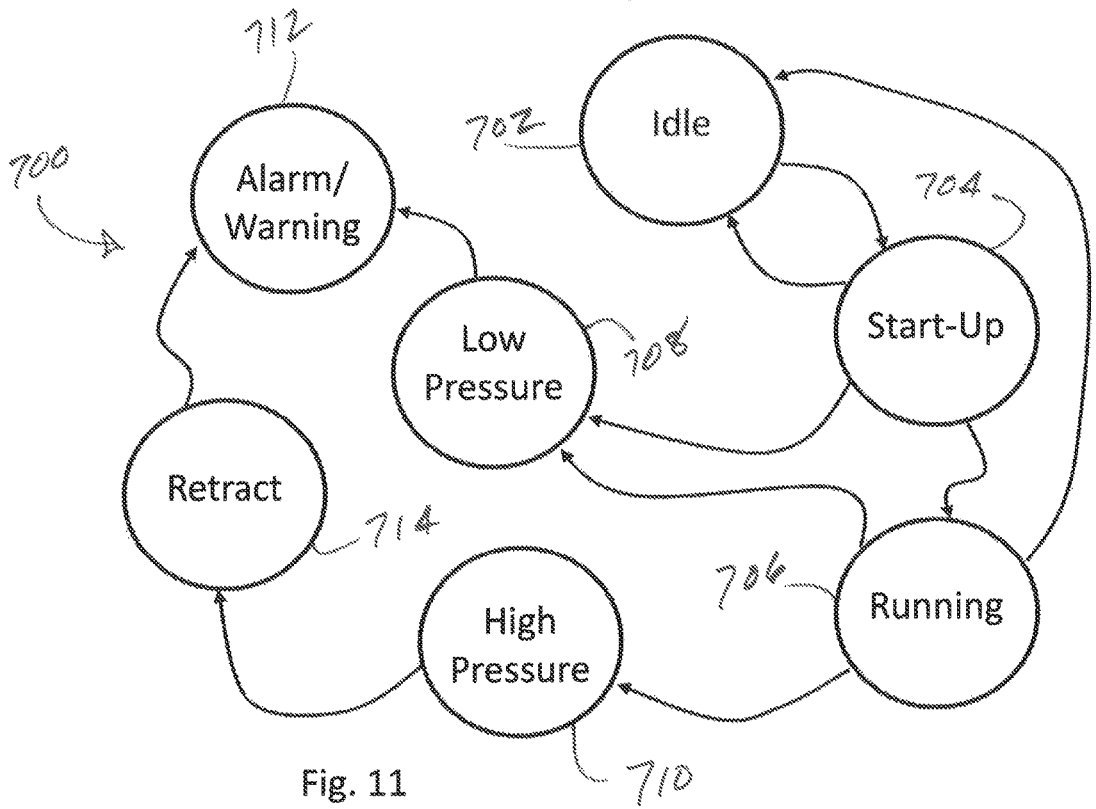
FIG. 11 is a state diagram that illustrates the behavior of the apparatus for injecting bone graft substitute and other materials considering all the possible states of the apparatus when an event occurs.

Referring now to FIG. 11 there is illustrated a state diagram, shown generally at 700, that illustrates the behavior of the apparatus 10 for injecting bone graft substitute and other materials considering the possible states of the apparatus 10 when an event occurs. This behavior is represented and analyzed in a series of events that occur in one or more possible states. Each balloon of the diagram represents objects and tracks the various states of these objects throughout the system. The state diagram 700 presents the same sequence of events of the method 600 from a different perspective.

The state system 700 allows the apparatus 10 to stop injection and reverse direction of the actuator 54 to alleviate high pressures when detected. The state system 700 also allows the apparatus 10 to detect pressure drops, in which case the injection system, by way of the actuator 54, shuts down and produces a warning so the user can take corrective actions as described above in conjunction with the method 600. The state system 700 also prevents false low pressure errors during the start-up phase of the system. State changes within the software are a function of the current state, the injection pressure, and the user input.

When the system is first turned on it is in the "idle" state 702. During this state the system is consuming minimal power. The purpose of this state is to wait for user input. When the user initiates operation of the system, such as by pressing the initiate button 24*a,* the system will transition into a Start-Up state 704. During this state the system will start running the actuator 54 and continue to build up pressure within the injection syringe 14 until the injection process will begin. Once the injection pressure passes a threshold value, the system will transfer to a Running state 706. If, however, the pressure does not raise above the threshold within a set time period the system will instead enter a Low Pressure state 708. The system will also be reset to the idle state 702 if at any time the user depresses the initiate button while in the Start-Up or Running state 704 and 706, respectively, or the injection process is completed. While in the Running state 706, the pressure will be continually checked and compared to an upper and lower pressure limit. If the injection pressure drops below the lower limit the system will change to the Low Pressure state 708. If the pressure increases too fast or rises above the upper limit, a High Pressure state 710 will be entered. The Low Pressure state 708 will set a flag within the system indicating the injection pressure was too low. After the flag is set, the system will transition into an Alarm/Warning state 712. Similarly the High Pressure state 710 will set a flag indicating the high pressure and transition into a Retract state 714. The Retract state 714 reverses the direction of the actuator 54 and reduces the pressure within the syringe 14 to a safe level. After this, the system will change to the Alarm/Warning state 712. While in the Alarm/Warning state 712, the user will be alerted to the high or low pressure error through either audio or visual cues. After the user responds to the problem and acknowledges the error, the system will reset to the Idle state 702.

The automated cement injection system achieves a reduction in force through the use of hydraulic and electrical components. The system also removes the need for manual manipulation to create the force for the injection. A microcontroller is used to control the system and allow for complete automation of the injection process. By removing the need for a surgeon to manually inject the cement both time and energy can be saved within the operating room. In addition, the automated cement injection system is able to calculate and display the pressure of the cement at the tip of the injection syringe. This pressure can be used to predict adverse effects from the cement injection. A low pressure will indicate to surgeons that the cement is leaking out of the desired area. A high pressure will inform that the cement is hardening, the injection site is filled or other anomalies. The system will automatically respond to these conditions and produce a warning as soon as one of these conditions results so that corrective actions can be taken immediately. This will help reduce complications normally associated with bone cement injection procedures.

The principle and mode of operation of this invention have been explained and illustrated in its preferred embodiment. However, it must be understood that this invention may be practiced otherwise than as specifically explained and illustrated without departing from its spirit or scope.

What is claimed is:

1. A metering delivery apparatus comprising:
   a body portion having a drive housing that supports an actuator drivetrain and receiver end;
   a material containment vessel configured to dispense a quantity of material and supported on the receiver end such that a portion of the vessel is secured to the body portion and another portion of the vessel is moveable relative to the body portion;
   an actuator having a first end connected to the actuator drivetrain and a second end configured to connect to and support the moveable portion of the vessel in both of a dispensing movement that exerts pressure on the material and a retracting movement that relieves pressure applied to the material; and
   a control unit that receives actuator parameter inputs and includes a sensor to detect a signal of at least one of a pressure level and a time period, the sensor providing the detected signal to the control unit such that the control unit operates the actuator between the dispensing and retracting movements based on the detected signal and the actuator parameter inputs;
   wherein the control unit includes a central processing unit (CPU) configured to receive the actuator parameter inputs and determine whether the detected signal is above or below a signal threshold value to operate the actuator and a display unit to display actuator operation parameters;
   wherein the control unit includes a current sensor circuit configured to monitor a power consumption level of the actuator; and,
   wherein the current sensor circuit detects at least one of an electrical current level flowing through the actuator and a voltage drop across the actuator during the dispensing and retracting movements, the circuit including an amplifier and a resistor, the CPU having an algorithm that determines the actuator power consumption from a voltage drop measurement from the actuator and a current level passing through the resistor.

2. The metering delivery apparatus of claim 1 wherein the material containment vessel is a syringe having a barrel with a barrel flange and a plunger with a plunger flange, the receiver end having a slot that engages the barrel flange to secure the barrel to the body portion, the actuator having a connection point that engages the plunger flange for actuation between the dispensing and retracting movements.

3. The metering delivery system of claim 1, wherein the amplifier is a high precision, single supply rail amplifier.

4. The metering delivery system of claim 1, wherein the display is a touch screen display supported on the body portion, the touch screen configured to receive user inputs and display performance information, the body portion further including a hand grip having an actuator drive switch that initiates movement of the actuator to dispense the material.

5. The metering delivery system of claim 4 wherein the actuator drive switch moves the actuator between an extended position corresponding to the dispensing movement and a retracted position corresponding to the retracting movement, the actuator drive switch forming an input signal to the CPU.

6. The metering delivery system of claim 5 wherein the CPU detects a power consumption level of the actuator to determine whether to maintain the dispensing movement or initiate the retracting movement.

7. A metering delivery apparatus comprising:
   a body portion having a drive housing that supports an actuator drivetrain and receiver end;
   a material containment vessel configured to dispense a quantity of material and supported on the receiver end such that a portion of the vessel is secured to the body portion and another portion of the vessel is moveable relative to the body portion;
   an actuator having a first end connected to the actuator drivetrain and a second end configured to connect to and support the moveable portion of the vessel in both of a dispensing movement that exerts pressure on the material and a retracting movement that relieves pressure applied to the material; and a control unit that receives actuator parameter inputs and includes a sensor to detect a signal of at least one of a pressure level and a time period, the sensor providing the detected signal to the control unit such that the control unit operates the actuator between the dispensing and retracting movements based on the detected signal and the actuator parameter inputs;

wherein the control unit includes a central processing unit (CPU) configured to receive the actuator parameter inputs and determine whether the detected signal is above or below a signal threshold value to operate the actuator and a display unit to display actuator operation parameters;

wherein the display is a touch screen display supported on the body portion, the touch screen configured to receive user inputs and display performance information, the body portion further including a hand grip having an actuator drive switch that initiates movement of the actuator to dispense the material;

wherein the actuator drive switch moves the actuator between an extended position corresponding to the dispensing movement and a retracted position corresponding to the retracting movement, the actuator drive switch forming an input signal to the CPU;

wherein the CPU detects a power consumption level of the actuator to determine whether to maintain the dispensing movement or initiate the retracting movement;

and wherein the control unit includes a current sensor circuit configured to monitor a power consumption level of the actuator, the current sensor circuit sensing a voltage drop measurement from the actuator and a current level passing through a resistor of the current sensor circuit.

8. A metering delivery apparatus comprising:

a body portion having a drive housing that supports an actuator drivetrain and receiver end;

a material containment vessel configured to dispense a quantity of material and supported on the receiver end such that a portion of the vessel is secured to the body portion and another portion of the vessel is moveable relative to the body portion;

an actuator having a first end connected to the actuator drivetrain and a second end configured to connect to and support the moveable portion of the vessel in both of a dispensing movement that exerts pressure on the material and a retracting movement that relieves pressure applied to the material; and a control unit that receives actuator parameter inputs and includes a sensor to detect a signal of at least one of a pressure level and a time period, the sensor providing the detected signal to the control unit such that the control unit operates the actuator between the dispensing and retracting movements based on the detected signal and the actuator parameter inputs;

wherein the material containment vessel is a syringe having a barrel with a barrel flange and a plunger with a plunger flange, the receiver end having a slot that engages the barrel flange to secure the barrel to the body portion, the actuator having a connection point that engages the plunger flange for actuation between the dispensing and retracting movements;

wherein the actuator drivetrain includes a hydraulic piston/cylinder assembly, the control unit including a central processing unit (CPU) configured to receive the actuator parameter inputs and determine whether the detected signal is above or below a signal threshold, the sensor being a pressure sensor; and, wherein the CPU includes an algorithm that determines whether the detected signal from the pressure sensor is above a low pressure level limit and receives a time period measurement of the dispensing movement of the actuator in response to the detected pressure sensor signal being less than the low pressure level limit, the CPU determining whether the time period measurement is below a time period threshold and maintaining the dispensing movement of the actuator in response to the time period measurement being less than the time period threshold.

9. The metering delivery system of claim 8, wherein the CPU includes an algorithm that determines whether the detected signal from the pressure sensor is below a high pressure level limit and continues to permit the dispensing movement of the actuator in response to the detected signal being below the high pressure level limit.

10. A metering delivery apparatus comprising:

a body portion having a drive housing that supports an actuator drivetrain and receiver end;

a material containment vessel configured to dispense a quantity of material and supported on the receiver end such that a portion of the vessel is secured to the body portion and another portion of the vessel is moveable relative to the body portion;

an actuator having a first end connected to the actuator drivetrain and a second end configured to connect to and support the moveable portion of the vessel in both of a dispensing movement that exerts pressure on the material and a retracting movement that relieves pressure applied to the material; and a control unit that receives actuator parameter inputs and includes a sensor to detect a signal of at least one of a pressure level and a time period, the sensor providing the detected signal to the control unit such that the control unit operates the actuator between the dispensing and retracting movements based on the detected signal and the actuator parameter inputs;

wherein the material containment vessel is a syringe having a barrel with a barrel flange and a plunger with a plunger flange, the receiver end having a slot that engages the barrel flange to secure the barrel to the body portion, the actuator having a connection point that engages the plunger flange for actuation between the dispensing and retracting movements;

wherein the actuator drivetrain includes a hydraulic piston/cylinder assembly, the control unit including a central processing unit (CPU) configured to receive the actuator parameter inputs and determine whether the detected signal is above or below a signal threshold, the sensor being a pressure sensor; and, wherein the control unit includes a current sensor circuit configured to monitor a power consumption level of the actuator, the current sensor circuit sensing a voltage drop measurement from the actuator and a current level passing through a resistor of the current sensor circuit, the CPU includes an algorithm that determines the actuator power consumption from a voltage drop measurement from the actuator and a current level passing through the resistor.

11. The metering delivery system of claim 10 wherein the CPU includes an algorithm that determines whether the detected signal from the pressure sensor is above a low pressure level limit and then whether the detected signal from the pressure sensor is below a high pressure level limit in response to the detected pressure sensor signal being greater than the low pressure level limit and continues to permit the dispensing movement of the actuator in response to the detected signal being below the high pressure level limit.

12. A metering delivery apparatus comprising:
a body portion having a drive housing that supports an actuator drivetrain and receiver end;
a material containment vessel configured to dispense a quantity of material and supported on the receiver end such that a portion of the vessel is secured to the body portion and another portion of the vessel is moveable relative to the body portion;
an actuator having a first end connected to the actuator drivetrain and a second end configured to connect to and support the moveable portion of the vessel in both of a dispensing movement that exerts pressure on the material and a retracting movement that relieves pressure applied to the material; and
a control unit that receives actuator parameter inputs and includes a sensor to detect a signal of at least one of a pressure level and a time period, the sensor providing the detected signal to the control unit such that the control unit operates the actuator between the dispensing and retracting movements based on the detected signal and the actuator parameter inputs;
wherein the material containment vessel is a syringe having a barrel with a barrel flange and a plunger with a plunger flange, the receiver end having a slot that engages the barrel flange to secure the barrel to the body portion, the actuator having a connection point that engages the plunger flange for actuation between the dispensing and retracting movements;
wherein the actuator drivetrain includes a hydraulic piston/cylinder assembly, the control unit including a central processing unit (CPU) configured to receive the actuator parameter inputs and determine whether the detected signal is above or below a signal threshold, the sensor being a pressure sensor; and,
wherein the hydraulic piston/cylinder assembly are a plurality of hydraulic piston/cylinder assemblies arranged to provide a force multiplying effect to the material containment vessel, the material containment vessel configured as a dual chamber vessel having a working fluid end and an injection syringe end.

13. The metering delivery system of claim 10, wherein the CPU includes an algorithm that determines whether the detected signal from the pressure sensor is below a high pressure level limit and continues to permit the dispensing movement of the actuator in response to the detected signal being below the high pressure level limit.

14. The metering delivery system of claim 12, wherein the CPU includes an algorithm that determines whether the detected signal from the pressure sensor is below a high pressure level limit and continues to permit the dispensing movement of the actuator in response to the detected signal being below the high pressure level limit.

* * * * *